US010060889B2

(12) United States Patent
Farnsworth et al.

(10) Patent No.: US 10,060,889 B2
(45) Date of Patent: Aug. 28, 2018

(54) LOW-POWER MINIATURE LED-BASED UV ABSORPTION DETECTOR WITH LOW DETECTION LIMITS FOR CAPILLARY LIQUID CHROMATOGRAPHY

(71) Applicant: BRIGHAM YOUNG UNIVERSITY, Provo, UT (US)

(72) Inventors: Paul B. Farnsworth, Orem, UT (US); Sonika Sharma, Provo, UT (US); H. Dennis Tolley, Mapleton, UT (US); Milton L. Lee, Pleasant Grove, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

(21) Appl. No.: 14/713,328

(22) Filed: May 15, 2015

(65) Prior Publication Data
US 2015/0330955 A1  Nov. 19, 2015

Related U.S. Application Data

(60) Provisional application No. 61/996,803, filed on May 15, 2014.

(51) Int. Cl.
*G01N 30/74* (2006.01)
*G01N 21/05* (2006.01)
(Continued)

(52) U.S. Cl.
CPC .......... *G01N 30/74* (2013.01); *G01N 21/05* (2013.01); *G01N 21/33* (2013.01); *G01N 2021/0346* (2013.01); *G01N 2201/0221* (2013.01); *G01N 2201/0621* (2013.01); *G01N 2201/0693* (2013.01)

(58) Field of Classification Search
CPC .......... G01N 30/74; G01N 21/05; G01N 21/33
See application file for complete search history.

(56) References Cited

U.S. PATENT DOCUMENTS 4,927,265 A   5/1990   Brownlee
5,124,020 A   6/1992   Wang
(Continued)

FOREIGN PATENT DOCUMENTS

CN   103529006       1/2014
EP   0616211         9/1994
WO   2013181362 A1   12/2013

OTHER PUBLICATIONS

Absorbance detector for high-performance liquid chromatography based on light-emitting diodes for the deep-ultraviolet range. Journal of Chromatography A 1218 (2011) 3750-3756 Bomastyk.
(Continued)

*Primary Examiner* — Hugh H Maupin
(74) *Attorney, Agent, or Firm* — Morriss O'Bryant Compagni Cannon, PLLC

(57) ABSTRACT

A system and method for performing UV LED-based absorption detection for capillary liquid chromatography for detecting and quantifying compounds in a liquid, wherein a simplified system eliminates the need for a beam splitter and a reference cell by using a stable UV source, and power requirements are reduced, resulting in a portable and substantially smaller system with relatively low detection limits.

24 Claims, 11 Drawing Sheets

(51) Int. Cl.
*G01N 21/33* (2006.01)
*G01N 21/03* (2006.01)

(56) References Cited

U.S. PATENT DOCUMENTS

| | | | |
|---|---|---|---|
| 5,235,409 A * | 8/1993 | Burgi | G01N 30/74 |
| | | | 204/452 |
| 5,533,063 A | 7/1996 | Mitra | |
| 2002/0123073 A1 | 9/2002 | Amirkhanian et al. | |
| 2003/0110840 A1 * | 6/2003 | Arriaga | G01N 15/1404 |
| | | | 73/61.72 |
| 2004/0070763 A1 | 4/2004 | Yeung | |
| 2005/0133724 A1 * | 6/2005 | Hsieh | B01L 7/52 |
| | | | 250/339.12 |
| 2006/0019265 A1 * | 1/2006 | Song et al. | 435/6 |
| 2006/0049051 A1 * | 3/2006 | Yeung | C07K 1/26 |
| | | | 204/450 |
| 2008/0013092 A1 * | 1/2008 | Maltezos et al. | 356/417 |
| 2008/0106736 A1 * | 5/2008 | Graves et al. | 356/338 |
| 2008/0304048 A1 * | 12/2008 | Tormod | G01N 21/05 |
| | | | 356/51 |
| 2010/0324830 A1 | 12/2010 | Solie | |
| 2012/0001094 A1 | 1/2012 | Killinger | |
| 2012/0252704 A1 | 10/2012 | Jaffe | |
| 2013/0284943 A1 | 10/2013 | Brukilacchio | |

OTHER PUBLICATIONS

LED-Based UV Absorption Detector with Low Detection Limits for Capillary Liquid Chromatography. Analytical Chemistry pubs.acs.org/ac Sharma.

Instrumentation for hand-portable liquid chromatography. Journal of Chromatography A 1327 (2014) 80-89 Sharma.

* cited by examiner

Sample cell and reference cell

LOW-POWER MINIATURE LED-BASED UV ABSORPTION DETECTOR WITH LOW DETECTION LIMITS FOR CAPILLARY LIQUID CHROMATOGRAPHY

BACKGROUND

Description of Related Art

Liquid chromatography (LC) is performed in order to analyze the contents of chemicals in a liquid solution. FIG. 1 shows that ultra-violet (UV) light 10 from a light source may be transmitted through a liquid 12 disposed within a capillary column 14 to a UV detector 16. The UV light may be absorbed by compounds in the liquid 12, leaving an intensity of light on the detector 16 that can be interpreted to detect and quantify compounds.

An example of a prior art system used for liquid chromatography (LC) is shown in FIG. 2. Standard UV light sources, such as a mercury (Hg) lamp 20, suffer from short lifespan, long warm-up time, and unstable light output. FIG. 2 shows that the light source may have to be split using a lens 22, resulting in a reduced light output of the source 20. The light source 20 may be split in order to go through a sample material 24 and a reference material 26 and the remaining light is then detected by a sample photocell 27 and a reference photocell 28 respectively.

New light sources may have been proposed that are more stable and produce less noise compared to standard UV light sources. Among these, light-emitting diodes (LEDs) have gained interest due to their long life, high stability, bright output and low power requirement. Additionally, they are small in size and more compact compared to standard light sources. Considering the nearly monochromatic behavior of LEDs, a monochromator is not required. An LED-based detector may be fabricated without using expensive optical lenses.

FIG. 3 is a block diagram of an LC detection system that uses an LED 30 as a light source. For LC, the UV range is desirable because many compounds that may be analyzed by LC exhibit absorption in that range. The prior art shows that light from a flat window LED 30 may be directly focused onto a flow-through cell and detection achieved using a signal photodiode 32. However, the detector 32 suffered from high noise, high detection limits and limited linearity. The system may have also suffered from high stray light levels. One problem with the LC detection system may be that silicon photodiodes 32 may be more sensitive at higher wavelengths than the UV, which may be evident from a photodiode sensitivity plot. Therefore, any light emission from an LED 30 at wavelengths higher than the UV may lead to significant stray light in the system. The system shown in FIG. 3 still required a beam splitter 33 which sent a portion of the light from the LED 30 to a reference diode 36. The other portion of the light was sent through a slit 34 and through a fused silica tubing 35. The detector 32 and the reference diode 36 were coupled as inputs to an amplifier 37.

Another prior art system used a hemispherical lens LED as a light source with a photomultiplier tube for on-capillary detection. This system may have suffered from a high level of stray light, which compromised the linear range and detection limits of the system.

Capillary columns have gained popularity in LC work, but a detector is needed that can fulfill the detection requirements for such columns. A prior art LC detection system using an Hg pen-ray lamp-based detector for on-capillary detection achieved good performance. However, commercial flow-cell based detectors may have introduced considerable dead volume for capillary columns. Furthermore, low-volume flow cells (few nLs) may be expensive and suffer from clogging problems due to salt deposition.

What is needed is a system that can provide narrow focusing of a light beam down to the internal diameter of the capillary column. One method of narrow focusing of light in order to eliminate stray light may be to use slits equal to or less than the capillary column internal diameter. However, the use of a slit in front of the capillary column also reduces the light throughput as shown in FIG. 3. A decrease in light intensity from the light source may decrease the S/N ratio of the detector.

BRIEF SUMMARY

The present invention is a system and method for performing UV LED-based absorption detection for capillary liquid chromatography for detecting and quantifying compounds in a liquid, wherein a simplified system eliminates the need for a beam splitter and a reference cell by using a stable UV source, and power requirements are reduced, resulting in a portable and substantially smaller system with relatively low detection limits.

These and other embodiments of the present invention will become apparent to those skilled in the art from a consideration of the following detailed description taken in combination with the accompanying drawings.

DETAILED DESCRIPTION

Reference will now be made to the drawings in which the various embodiments of the present invention will be given numerical designations and in which the embodiments will be discussed so as to enable one skilled in the art to make and use the invention. It is to be understood that the following description illustrates embodiments of the present invention, and should not be viewed as narrowing the claims which follow.

Before beginning, it should be understood that on-column detection may refer to when packed bed material terminates before the end of the column so that the last part of the column is actually empty. But there may also be situations in which the column has packed bed material all the way to the end of the column and a capillary has to be added in order to perform detection in the capillary portion. Accordingly, the embodiments of the invention should all be considered to include both configurations to be within the scope of all embodiments, where detection is taking place on-column in an area of the column that does not contain packed bed material, or within a capillary that has been added to the very end of the column where the packed bed material ends.

A first embodiment is an LED-based UV absorption detector with low detection limits for use with capillary liquid chromatography. In a first aspect of the first embodiment, an LED light source may be selected. The LED output wavelength may change with changes in drive current and junction temperature. Therefore, LEDs should be driven by a constant current supply, and heating of the system should be avoided.

The quasi-monochromaticity of the LED source contributes to stray light in the system, leading to detector non-linearity. The detection system should be protected from any LED light outside the desired absorption band by employing a filter in the system.

On-column capillary detection may be preferred for capillary columns, since narrow peak widths are obtained by eliminating extra-column band dispersion, and peak resolution is maintained. The short-term noise in the detector may determine the detection limits and may be generally reduced by performing integration, smoothing, and/or using low-pass RC filters.

The first embodiment shows that UV LED-based absorption detectors have great potential for miniaturization for field analysis. Further optimization of the detector design and reduction in the noise level may lead to better detection limits for small diameter capillary columns. The first embodiment resulted in a hand-portable 260 nm LED based UV absorption detector specifically for capillary LC on-column detection. The system is relatively small, lightweight and has very low power consumption compared to the prior art.

Figure 4:
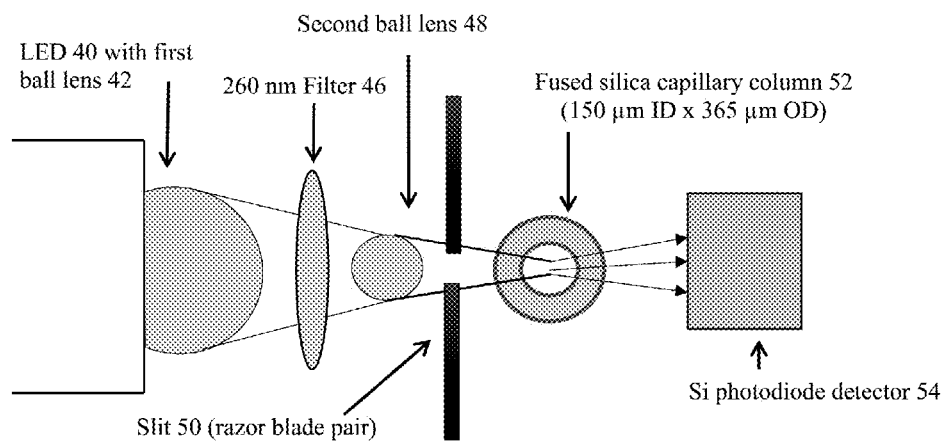
FIG. 4 is a first schematic diagram of a first embodiment of the invention showing the major hardware elements of a capillary LC system.

FIG. 4 is a first schematic diagram for introducing the elements of the first embodiment of the invention. The elements include a UV-based LED 40, a first ball lens 42, a band-pass filter 46 that is tuned to the LED 40 light source, a second ball lens 48, a slit 50 comprised of razor blades, a capillary column 52 that may have an inner diameter (ID) of approximately 150 μm and an outer diameter of approximately 365 μm, and a silicon photodiode detector 54.

Figure 1:
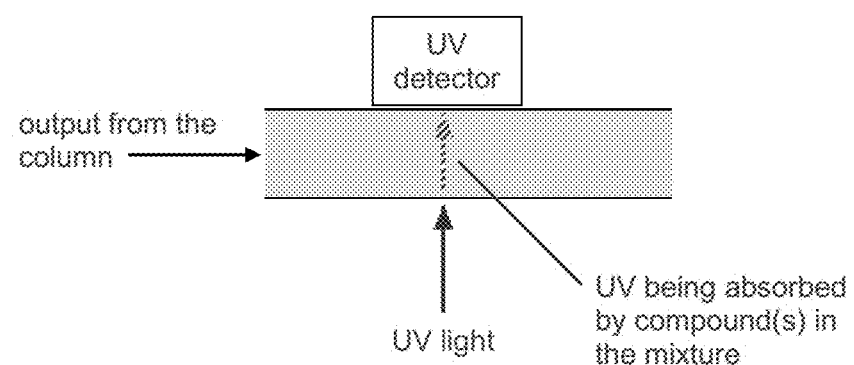
FIG. 1 is a diagram showing the operation of a UV detection system where UV light is passed through a capillary column.
Figure 2:
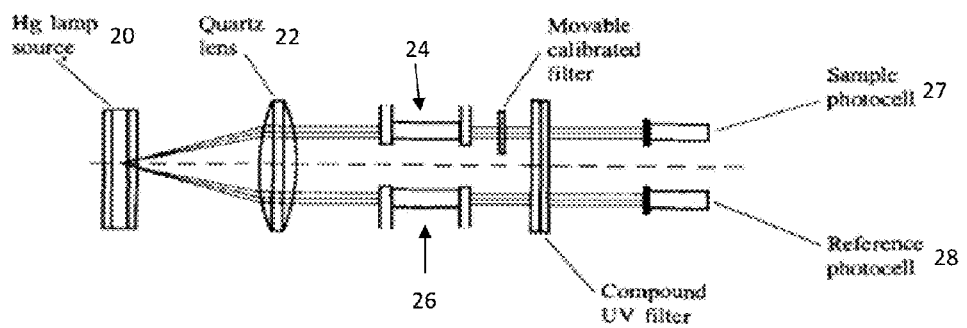
FIG. 2 is a diagram showing a prior art detection system for generating a sample light source and a reference light source using a beam splitter and an Hg light source.
Figure 3:
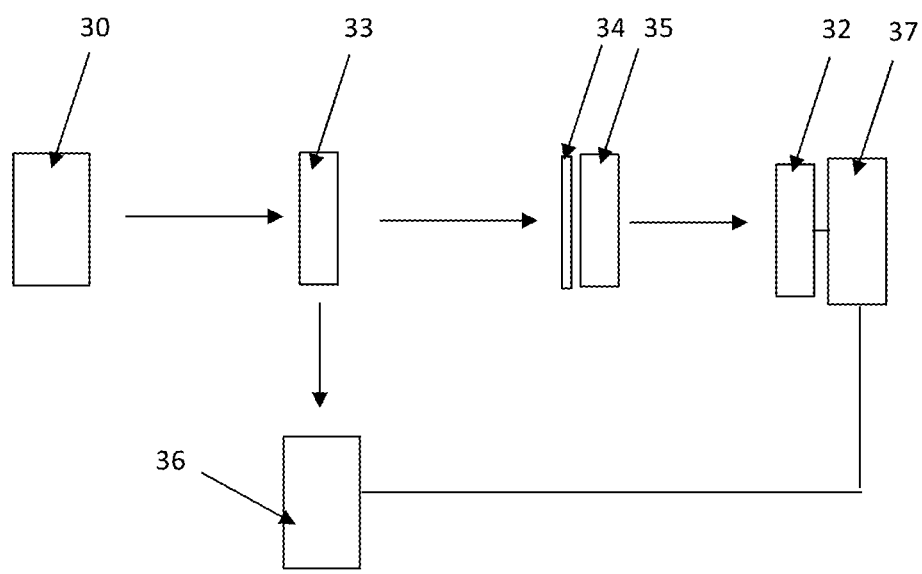
FIG. 3 is a diagram showing an alternative prior art detection system that uses a UV LED as a light source, but which still uses a beam splitter to create a reference source but which suffers from reduced UV light intensity.

The scale of the elements of the invention are not shown in FIG. 4. The UV light from the second ball lens 48 may be converging much more sharply than shown. Furthermore, the diameter of the second ball lens 48 may be more than 10 times larger than the inner diameter of the capillary column 54. Accordingly, it should be understood that FIGS. 3 and 4 are provided to show the physical order of the components of the invention without showing the actual sizes.

In addition, it should be understood that any drawings of the convergence of UV light caused by the first and second ball lenses 42, 48 is not being shown to scale and is for illustration purposes only.

It may be possible to provide the same functionality as the components of the detection system listed above by substituting other components that provide the same function. For example, while a first and second ball lens 42, 48 are shown in FIG. 4, a different type of lens may be substituted and should still be considered to fall within the scope of the first embodiment. It may also be possible to provide the functionality of the first two ball lenses using a single lens and obtain the desired focusing effect. It should also be understood that the values to be given for all aspects of the first embodiment are approximate only and may vary up to 50% without departing from the desired functionality of the first embodiment.

Figure 5:
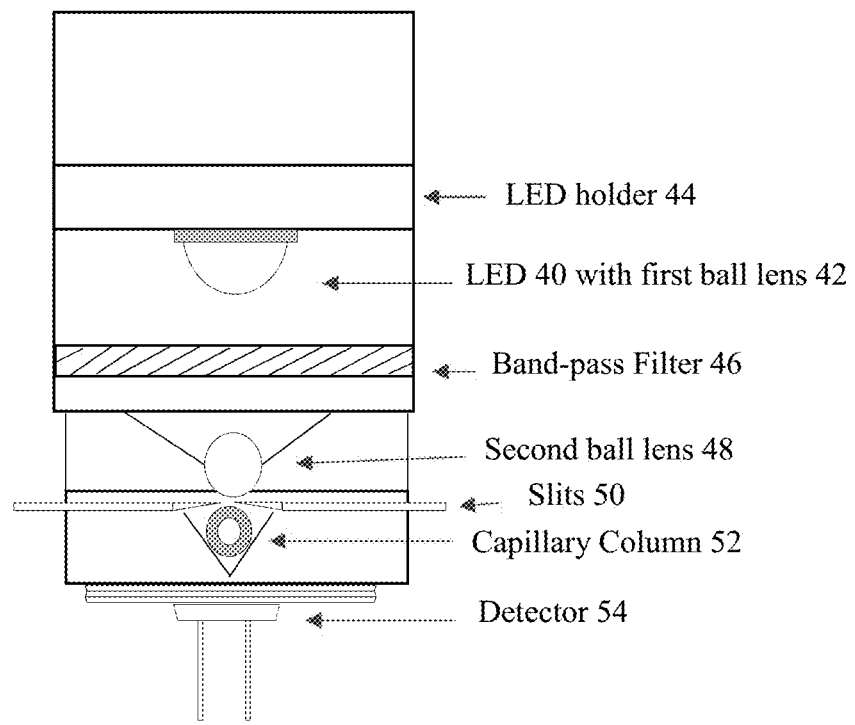
FIG. 5 is a second schematic diagram of the first embodiment of the invention showing more construction detail of a capillary LC system.

FIG. 5 is a cut-away profile view of the first embodiment shown with more construction detail. This system shown in FIG. 5 should not be considered as limiting of the invention, but as a demonstration of the principles of the first embodiment. Accordingly, specific values given for size, shape, weight, power, sensitivity or any other characteristics of components of the first embodiment are for example only and may vary from the values given.

FIG. 5 shows an LED 40 having a first ball lens 42. The LED 40 may be disposed within an LED holder 44. The LED 40 may be manufactured as integrated with the first ball lens 42, or it may be attached or disposed adjacent to the first ball lens 42 after manufacturing. The LED 40 may be selected from any desired bandwidth of UV light that is appropriate for the compounds being analyzed in the capillary column 52. The first embodiment uses a 260 nm LED 40, but this wavelength of UV light may be changed as desired.

In the first embodiment, a commercially available 260 nm UV LED 40 with a first ball lens 42 was used as a light source. The LED 40 was mounted on the LED holder 44. The LED holder 44 was threaded into a black lens tube and held tight with the help of retaining rings. The first ball lens 42 may be 6 mm in diameter, or any appropriate size to focus the light from the LED 40.

The first embodiment includes a band-pass filter 46 disposed after the first ball lens 42. The band-pass filter 46 may be a 260 nm band-pass filter used to reduce stray light from reaching a detector from the LED 40 and/or any surrounding light. The value of the band-pass filter may be adjusted as needed in order to be optimized for the LED 40 light source.

In the first embodiment, a 260 nm band-pass filter may be positioned in between the LED 40 and the second ball lens 42 in the black threaded tube.

Another element of the first embodiment may be the use of a second ball lens 48 disposed after the band-pass filter 46. The function of the second ball lens 48 may be to receive the UV light that is focused by the first ball lens 42 and focus the UV light even further. It is desirable to focus the UV light so that the light sent into the capillary column 52 may be equal to or smaller than the width of the inside diameter (ID). While it is preferred, the focusing of the UV light source may not be equal to or smaller than the ID of the capillary column 52 in the first embodiment.

In the first embodiment, a fused silica ball lens may have a 3 mm diameter for the second ball lens 48 and may be mounted on a 3 mm ball lens disk and may be disposed at the LED focal point. The second ball lens mount may be centered on a mount, which may be threaded into the black lens tube containing the LED 40 and the band-pass filter 46.

With increased light throughput through the capillary column 52 and received by the detector, it was experimentally determined that light intensity incident on the detector may be up to three orders of magnitude higher than prior art capillary LC designs.

To reduce stray light reaching the detector 54, one or more slits 50 are disposed after the second ball lens 48 and in front of the capillary column 52. The slits 50 may be provided by razor blades or any other appropriate device. The slits may be approximately 100 μm in width.

The combination of the band-pass filter 46 and the slits 50, stray light was experimentally reduced to a value of 3.6%, which is very low compared to prior art systems that may operate at reductions of stray light to a value 30.5%. Prior art designs may have either used special UV index photodiodes for higher wavelength stray light elimination which apparently were not very effective, or may have used a slit (100 μm width) in front of 250 μm ID hollow capillary connected to the end of a commercial column (1 mm ID). This led to reduced light throughput through the capillary column 52. Furthermore, band broadening due to a connection between a larger diameter tube to a smaller diameter tube impairs detection sensitivity.

The UV light that passes through the capillary column 52 is positioned so that it strikes a UV detector 54. The UV detector 54 may be any UV sensitive device.

In the first embodiment, the UV detector 54 may be a silicon photodiode. The photodiode 54 may be disposed on a diode holder with external threads. A black cap may be built to thread into the diode holder. This black cap may have a V-shaped groove to hold the capillary column 52 in the center, a central hole to allow light passage, and grooves on opposite sides of the hole to hold the slits in place. A pair of razor blades may be used to fabricate the adjustable slit or slits 50. The slits 50 may be disposed on opposite sides of the central hole in the cap covering the outer diameter of the capillary column longitudinally.

In the detector 54, an operational amplifier may be used to receive the current from the photodiode and convert it into voltage values. An analog-to-digital converter may be used to record the voltage output with a computer or other recording device. It should be understood that a low pass RC filter may be used at the input to the analog-to-digital converter.

The examples to follow show experimental values for the first embodiment only and should not be considered as limiting performance thereof. Data points were sampled at a rate of 1 KHz to 42 KHz. These data points were then smoothed at a 10 Hz rate to reduce the noise level in the detection system. These values should not be considered as limiting, but serve to illustrate the principles of the embodiments of the invention. The data point sampling rate and data smoothing rate may be adjusted in order to optimize results for the detection system being used.

The LED 40 and silicon photodiode detector 54 may require 6 V and 12 V DC power, respectively, for operation. The detector 54 required 0.139 Amp current, and could operate for approximately 25 hours using a 4 Amp-hour 12 V DC battery, as well as operate from line power with an AC to DC adapter. However, it should be understood that the detection system of the first embodiment may operate using a DC power source and therefore may be portable not only because of the DC power requirements, but because of the relatively small dimensions of the detection system.

An integrated stop-flow injector with an injection volume of 60 nL was used in these experiments, unless otherwise specified. A 150 μm ID×365 μm OD Teflon-coated capillary column 52 was used in all experiments. The absorbance values, where reported, were calculated by taking the common logarithm of the inverse of the transmittance values. The transmittance was calculated by dividing the sample signal by the reference signal obtained by recording the baseline.

Detector noise was determined over 1-min measurements of baseline data. A hollow fused silica capillary was connected to a nano-flow pumping system and filled with water. The baseline was then recorded for approximately 1 min, and the peak-to-peak absorbance was calculated. This gave the peak-to-peak (p-p) noise. Short term noise (RMS) was calculated as the standard deviation of the recorded baseline. For dark noise measurements, the LED 40 was turned off and the dark noise was measured as the standard deviation in the baseline. To determine digitizer noise, the positive and negative terminals of the A/D converter were shorted. Detector drift was determined by flowing water through the capillary at 300 nL/min and recording the baseline for 1 h, followed by measuring the slope of the baseline.

Software smoothing was performed to reduce the noise level. However, it should be understood that the smoothing function may be performed in hardware at a faster rate and may be substituted for the software smoothing. Although we can use a variety of smoothing techniques, the smoothing technique used in the first embodiment is fixed window averaging. Other smoothing techniques that may be used include but should not be considered as limited to, smoothing by averaging over a sliding window of fixed width, smoothing using an exponentially weighted moving average, and smoothing using a causal or non-causal filter constructed to whiten the baseline noise process.

Using a 150 μm ID capillary column 52 and 5.35 pmol injections of uracil in solution, the S/N ratio was determined at different smoothing rates, and the best smoothing rate was used for further work. The effect of RC filters (time constants of 0.5 s and 1 s) on short-term noise was also studied with and without performing any smoothing. A black ink-filled capillary was used for stray light assessment in the system. The stray light level was measured by dividing the voltage signal obtained for black-ink conditions by the voltage signal obtained with a water-filled capillary column 52, multiplied by 100.

Solutions of different concentrations of sodium anthraquinone-2-sulfonate (SAS), adenosine-5-monophosphate (AMP), DL-tryptophan (DLT) and phenol were made in HPLC grade water. Solutions were made to flow, under nitrogen pressure, through a capillary inserted into the detector 54. Baseline data were recorded before and after each concentration experiment by flowing water through the capillary. Baseline corrected maximum absorbance unit (AU) values were plotted against molar concentrations (M) to determine the linearity of the detector 54. Detection limits for flow-through experiments were reported as 3 times the standard deviation in the baseline. Log-log plots were used to determine the sensitivity of the detector 54. Calibration data for phenol were also obtained by making injections on a PEGDA monolithic column, and baseline corrected peak areas were plotted against concentrations. Elution conditions were as described in the next paragraph. Detection limits were determined as 3 times the standard deviation in the baseline area obtained from blank injections (n=4) and calculated within the analyte peak zone.

Isocratic separations of phenols (i.e., phenol, catechol, resorcinol and pyrogallol) were performed using a PEGDA monolithic capillary column 52 (16.5 cm×150 μm ID) using the integrated system. The pretreated capillary column 52 was filled with monomer mixture and subjected to UV-initiated polymerization for 5 min. After polymerization, the monolithic column was washed with methanol followed by water for at least 6 h to remove unreacted compounds. The monomer mixture composition was: DMPA (0.002 g), PEGDA 700 (0.2 g), dodecanol (0.15 g), decanol (0.15 g), decane (0.2 g) and tergitol 15-S-20 (0.3 g). The phenolic compounds were dissolved in HPLC water and the mobile phase was 80/20% (v/v) acetonitrile/water mixture. Separations were performed at 350 nL/min.

The UV LED-based absorption detector 54 may be much smaller than an earlier described Hg pen-ray lamp-based detector. For on-capillary column detection, absorbance values may be small, so noise reduction may be important to obtaining good detection limits. A bright light source LED 40 may increase the photocurrents used to calculate absorbances without proportional increase in noise. A single wavelength (260 nm) detector 54 was fabricated instead of a multi-wavelength detector in order to reduce the cost and size of the detection system.

Although the LED 40 had an integrated fused silica first ball lens 42 (6.35 mm diameter), which focused the light beam down to a 1.5-2.0 mm spot at the focal point (15-20 mm), this was still too broad for the capillary column 52 dimensions (0.075 to 0.20 mm ID). Therefore, the second fused silica ball lens 48 (3 mm diameter) was placed at the focal point of the LED 40 to obtain improved focusing of the light. The first and the second ball lenses 42, 48 may be constructed of any appropriate material.

The LED 40 was selected to emit light with a bandwidth of ±5 nm; however, with a spectrometer, it was determined that the LED emitted light at higher wavelengths as well. The additional wavelengths of light may have contributed significantly to the stray light of the system.

Figure 6:
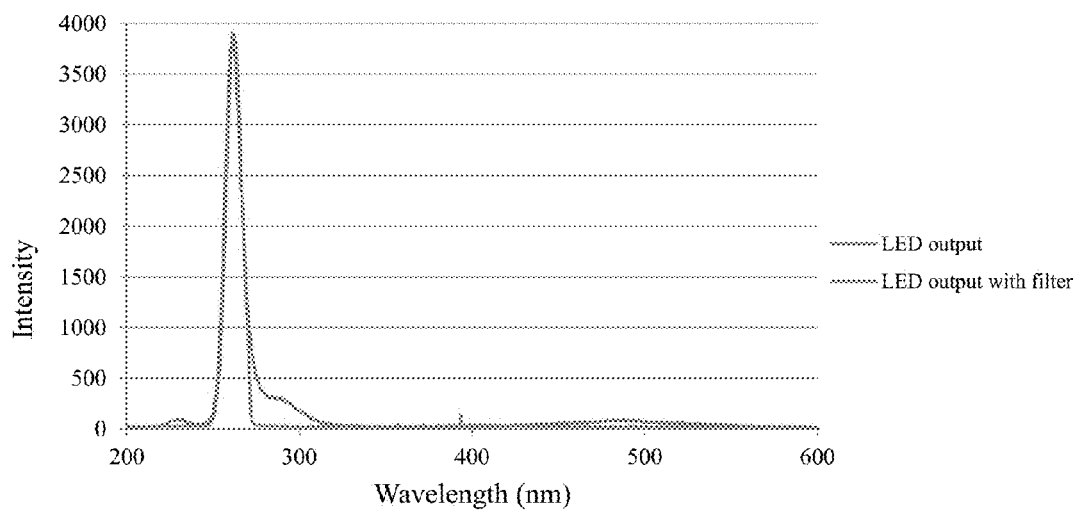
FIG. 6 is a graph of overlaid spectra of light output with (orange) and without (blue) a filter.

A 260 nm band-pass filter with a FWHM of 20 nm was used during experimentation. The overlaid spectra in FIG. 6 show the light output from the LED 40 with and without the filter, confirming that the filter successfully eliminated the light from higher wavelengths. The LED 40 position was optimized to obtain the best focus at the center of the capillary column 52.

Due to the reported inherent stability of the LED 40, a reference cell was eliminated from the design of the first embodiment. Elimination of the reference cell also resulted in elimination of a beam splitter in the first embodiment, which elimination increases the UV light throughput through the capillary column 52. Since no other optical lenses except the first and second ball lenses 42, 48 were used, complex alignment of optical elements and transmission losses from multiple surfaces were also avoided in the first embodiment.

Figure 7:
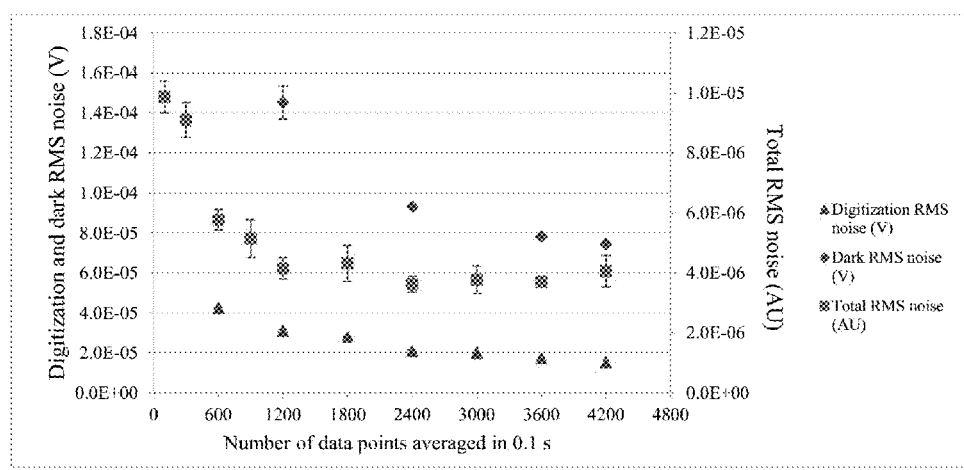
FIG. 7 is a graph of the effect of software smoothing on digitization and dark RMS noise without filter and on the total RMS noise with 0.5 s filter.

A feature of the first embodiment that is part of the functionality of the detector 54 is to perform processing of the detection data. In the experimental use of the first embodiment, the short-term RMS noise of the detector 54 was found to be 8 mV without the use of signal smoothing and low pass filter. The dark RMS noise without smoothing was calculated to be 6.95 mV. Software smoothing reduced the dark RMS noise level to 74.4 $\mu$V as shown in FIG. 7. The dark voltage values were the same in a lighted and dark room, confirming that the capillary column 52 did not act as a light guide. Digitizer noise can contribute significantly to the minimum noise obtainable with a detector. The digitizer RMS and p-p noise were found to be 2.4 mV and 7.7 mV, respectively. The effect of software smoothing on the digitizer RMS noise was studied as shown in FIG. 7 and the minimum RMS and p-p noise levels obtained were 15 $\mu$V and 95 $\mu$V, respectively.

As can be seen from the data, dark current noise, which includes noise from the photodiode and amplifier, and digitizer noise both contributed to the total baseline noise, and both were effectively reduced using software smoothing of the first embodiment. To further reduce the total noise level, two low-pass filters (time constant=0.5 s and 1 s) were applied to the input of the A/D converter. The unaveraged RMS noise level dropped to 2.42 mV and 2.3 mV, respectively.

The effect of software smoothing on the S/N ratio was also studied and, while it was found that the effect of smoothing on the signal intensity for peak widths in the chromatogram was negligible, the RMS noise level was reduced to a level of 0.18 mV in the voltage corresponding to intensity of incident light (Io) (5.7 $\mu$AU) without the use of a filter. With a 0.5 s filter and 4200 data points per 0.1 s smoothing, the RMS noise further dropped to 0.14 mV (4.4 $\mu$AU). Thus, the LED detector RMS noise was an order of magnitude lower (~$10^{-6}$ AU) than previous detectors and other UV LED detectors (~$10^{-5}$ AU). The detector 54 drift was found to be very low ($10^{-5}$ AU per h), which may be negligible over a peak width and may present no problems for the duration of a typical chromatogram.

Figure 8:
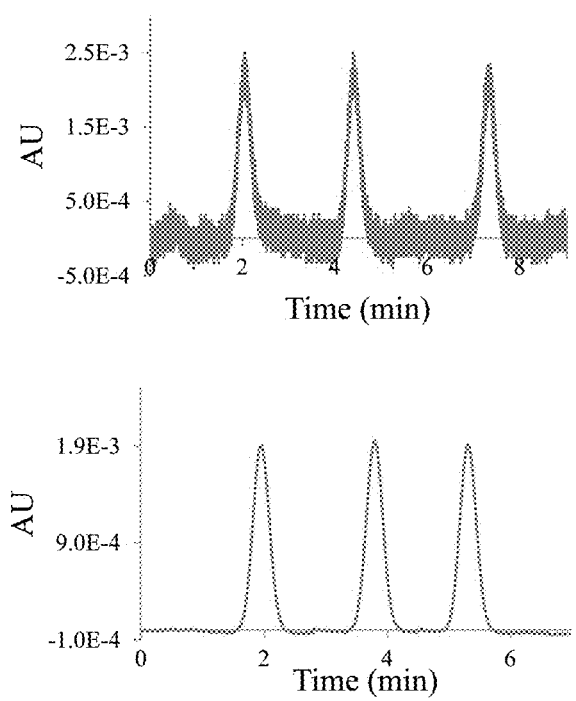
FIG. 8 shows two graphs that illustrate S/N ratio enhancement of the first embodiment, where signals were obtained (A) without smoothing and (B) with 4200 data points per 0.1 s smoothing.

As can be seen in FIG. 7, the RMS noise level decreased as the number of data points averaged per 0.1 s was increased from 100 to 2400; however, further decrease in the noise level after 2400 data points smoothing was not significant. The S/N ratio for uracil increased from 14 (without smoothing) to 408 (with 4200 data points smoothing) as shown in FIG. 8. Due to the reported and observed low drift and inherent light stability of the LED, a reference cell was not included, simplifying the detector 54 design of the first embodiment without compromising its performance. The photodiode signal through the capillary column 52 (an average of 70 $\mu$A) was three orders of magnitude higher than previous work (nA range).

Stray light may cause negative deviations from true absorbance values. When the slit 50 width was adjusted to be equal to the internal diameter of the capillary column 52 (i.e., 150 $\mu$m), the stray light level was measured to be 17.3%. By visual inspection, it was found that a significant level of light reached the detector 54 through the curved capillary column 52 wall. Therefore, the slit 50 width was reduced to 100 $\mu$m, which reduced the stray light level to 3.6%. A decrease in light intensity was compensated for by increasing the driving current on the LED 40 (13.3 mA). Therefore, the output voltage signal intensity was not compromised at all by a reduction in the slit 50 width.

During experimentation, the LED 40 was operated at only half of its maximum operating current. The maximum absorbance of the detector 54 with the capillary was calculated to be 1.4 AU, which is higher than the value obtained with the Hg pen-ray lamp detector (0.94 AU).

The linearity of a UV absorption detector may be compromised by improper focusing of the light source on the ID of the capillary column 54. Limits of detection depend on detector 54 short-term noise and the test analyte molar absorptivity. For the experiment, selection of test analytes was based on molar absorptivities and relevant previous LED detector work. The detector 54 gave a linear response up to the highest concentration tested, confirming that stray light was low in the system. The linear dynamic range was three orders of magnitude for all of the test analytes. The limit of detection at a S/N ratio of 3 was found experimentally to be 24.6 nM (7.63 ppb) or 1.5 fmol for SAS. This detection limit may be five times lower than a prior art pen-ray Hg lamp-based detector.

Considering that anthraquinone and anthracene exhibit similar molar absorptivities, this detection limit is also three times lower than the non-referenced single-wavelength flow cell-based (1 cm long) detection limit reported earlier. The detection limits for AMP (87.9 nM or 30.5 ppb) would be 230 times lower for the same capillary column 54 dimensions (75 μm ID) than a non-referenced LED detector reported earlier. For DLT, the detection limit at an S/N ratio of 3 was found to be 299 nM (61 ppb) or 17.9 fmol. This detection limit would be 60 times lower than the referenced detector reported earlier for the same capillary dimensions (250 μm ID. Thus, the variations in detection limits for the various compounds is consistent with the variations in molar absorptivities at 260 nm.

The detection limits for the detector 54 are remarkable considering the fact that detection was performed on the capillary scale. The calibration data for SAS, AMP and DLT are listed in Table 1. The RSDs in peak areas (n=3) for the three compounds ranged from 0.4-2.6%. These areas were calculated by injecting different concentrations of each compound three times into a hollow capillary column using water as carrier fluid at 600 nL/min.

Using on-column detection may improve peak shapes and increase detection sensitivity because extra-column band broadening may be reduced.

Figure 9:
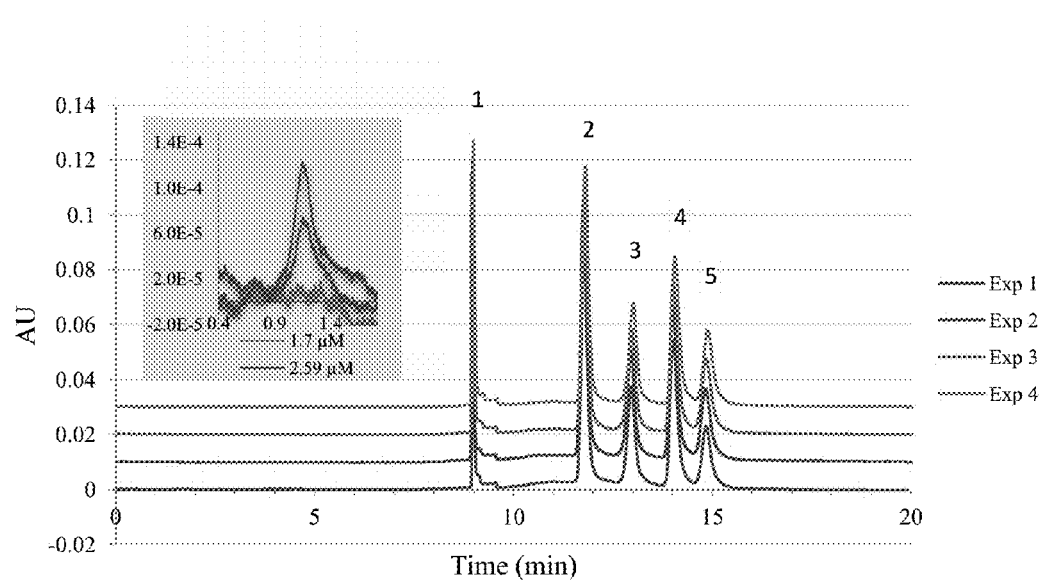
FIG. 9 is a graph showing separations using integrated nano-flow pumping system and LED detector.

Application of the capillary LC system was demonstrated using phenolic compounds as shown in FIG. 9. Good resolution was obtained for all analytes in an isocratic mode. Baseline stability under LC experiments was remarkable, confirming the low drift exhibited by this detector. The retention times in min and peak widths in s (tR/wb1/2) of the compounds were found to be: phenol (11.79/10.4), catechol (12.98/13.4), resorcinol (14.03/12.8) and pyrogallol (14.85/16.6). The reproducibility of peak retention times ranged from 0.1-0.2% (n=4). The column efficiencies (N/m) and minimum plate heights (μm) for the retained compounds were: phenol (156,838/6.4), catechol (113,118/8.8), resorcinol (144,673/6.9) and pyrogallol (96,963/10.4).

The first embodiment may be a highly sensitive on-column detector 54 fabricated using a 260 nm UV LED 40 that can detect in the ppb range. The noise level of the detector 54 was remarkably reduced by the use of software smoothing and a low pass filter, i.e., 3.4-4.4 μAU, which is among the lowest noise levels ever attained with absorption detectors designed for capillary column 52 work. The low detection limits may be attributed to good light focusing, low stray light, and very low noise in the system.

TABLE 1

| Analytes | Concentration range | Peak area (AU) Regression equation | $R^2$ | Sensitivity[d] | LOD |
|---|---|---|---|---|---|
| SAS | 24.6 nM-50.4 μM | y = 498.09x + 9 × 10$^{-6}$ | 1[a] | 0.9968 | 24.9 nM |
| AMP | 87.9 nM-22.5 μM | y = 185.44x + 5 × 10$^{-6}$ | 0.9999[b] | 1.0138 | 87.9 nM |
| DLT | 299 nM-0.61 mM | y = 54.744x + 5 × 10$^{-6}$ | 1[c] | 0.9855 | 299 nM |

[a]For n = 12;
[b]For n = 9;
[c]For n = 12;
[d]Sensitivity was obtained using log (AU) vs log (M) plots.

Since the detector 54 is specifically designed for on-column detection, the detector performance was tested under LC conditions using phenol and compared with the flow-through experiments as shown in Table 2. The detector linearity was excellent under both conditions, and the detection limits were found to be similar. Hence, the detector performance was not compromised when used under actual LC conditions.

TABLE 2

| Method | Concentration range | Peak area (AU) Regression equation | $R^2$ | LOD |
|---|---|---|---|---|
| Flow-through | 1.95 μM-1.33 mM | y = 14.252x + 2 × 10$^{-5}$ | 1 | 1.95 μM |
| On-column | 1.70 μM-1.33 mM | y = 3118.9x + 0.0121 | 0.9997 | 1.96 μM |

Capillary LC is performed by the first embodiment of the invention. Accordingly, the detection system includes a system for analyzing absorption of the UV light by at least one compound disposed in a liquid within the capillary column by analyzing the UV light that is received by the detector. The system for analyzing absorption may be part of the detector or may be a computer system that is coupled to the detection system for receiving data from the detector.

It is also noted that the first embodiment performs on-column LC detection using a monolithic capillary column.

The low detection limits of the first embodiment may be obtained for the test compounds due to the good light focusing, low stray light and very low noise in the capillary LC system. The detection limits for SAS in the capillary format with 150 μm pathlength may be 3 times lower than the LED-based detector with 1 cm pathlength. For AMP and DLT, the detection limits were improved by a factor of 230 and 60 in comparison with the detectors with the same pathlength. Also, phenol detection limits in our detector were the same under flow-through experiments and under separation conditions. Thus, detector performance was not compromised under actual liquid chromatography work. Reproducible isocratic separation of a phenol mixture was also demonstrated.

Software smoothing was used to reduce the noise level in the detection system. Without smoothing, the total root mean square noise level was 8 mV. With the 4200 data points per 0.1 second smoothing, the noise level was reduced to 0.18 mV and when a low pass RC filter (2 Hz time constant) was employed to the input of the analog-to-digital converter, the noise further reduced to 0.14 mV (equivalent to 4.4 μAU). This is one of the lowest noise levels ever attained with capillary based detectors. Without software smoothing and using just the RC filter, the noise level was only reduced from 8 mV to 2.4 mV. Thus, low-pass filtering was clearly not enough to effectively eliminate high frequency noise from the detection system. The S/N ratio increased from 14 to 408 for 5.35 pmol uracil peaks. The noise level was up to 2 orders of magnitude smaller than the prior art in which some detectors only relied on a low pass filter.

A final comment regarding the size, weight, power requirements and portability of the first embodiment are a direct result of the uncomplicated design of the capillary LC system. A typical commercial system may have size dimensions of 11×13×22 cm, have a weight of 3.3 lbs., require a regular AC power line, and have a sensitivity that is approximately 1 mAU. In contrast, the first embodiment may have dimensions that are approximately 5.2×3×3 cm, may have a weight of 0.2 lbs., may operate from a 12 DC power source and only use 1.68 W, and may have a sensitivity of approximately 10 μAU. It should be understood that these values are approximate only and may vary up to 50% without departing from the characteristics of the first embodiment.

Figure 10:
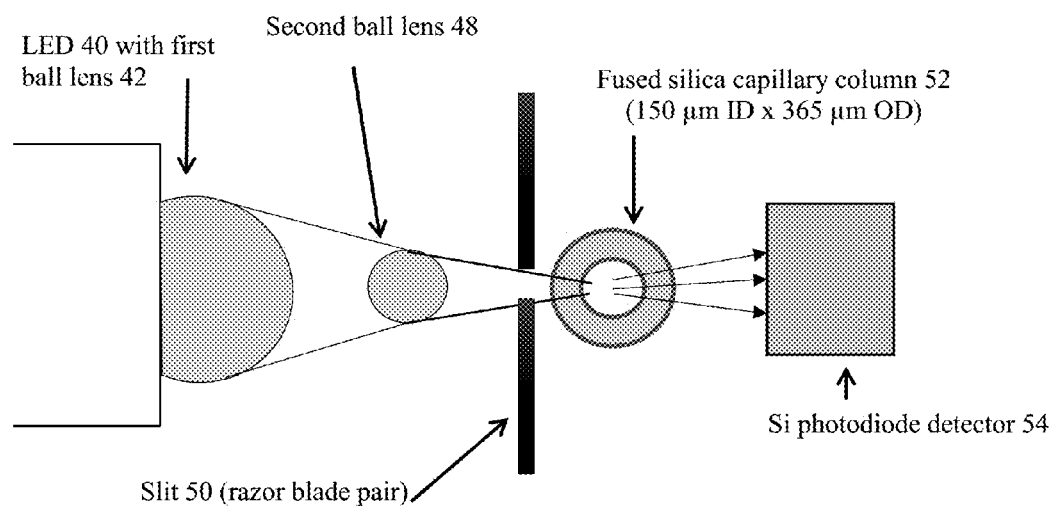
FIG. 10 is a block diagram of the components in a second embodiment of the invention.
Figure 11:
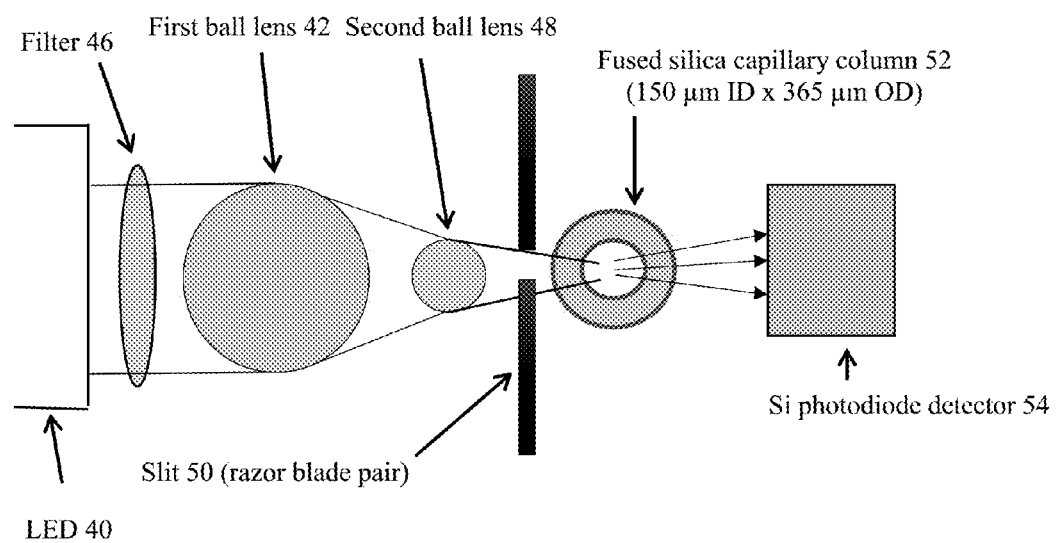
FIG. 11 is a block diagram of the components in a third embodiment of the invention.

FIGS. 10 and 11 are provided as a second and third embodiments of the invention. Specifically, all features and functionality of the second and third embodiments are the same as the first embodiment, with the exception of a change in the order of the first ball lens 42, the filter 46 and the second ball lens 48. FIG. 10 illustrates in a diagram that it may be possible to position the first ball lens 42 adjacent to the second ball lens 48, and to then eliminate the filter 46 entirely.

The filter 46 may eventually become unnecessary if the UV light source can be made more perfectly monochromatic. Filtering is performed in order to prevent any stray light from reaching the capillary column 54. If no or very little stray light is generated by the UV light source, then the filter becomes unnecessary and may be removed from the system without departing from the principles of the present invention.

In contrast, FIG. 11 illustrates in a diagram that it may be possible to position the filter 46 between the LED 40 and the first ball lens 42, and then position the second ball lens 48 adjacent to the first ball lens as in FIG. 10. In other words, it may be possible to dispose the filter 46 in front of both ball lenses 42, 48, and between the ball lenses, or eliminate the filter entirely and still achieve the desired focusing and filtering of the UV light from the LED 40.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. It is the express intention of the applicant not to invoke 35 U.S.C. § 112, paragraph 6 for any limitations of any of the claims herein, except for those in which the claim expressly uses the words 'means for' together with an associated function.

What is claimed is:

1. An ultra-violet (UV) light emitting diode (LED) based absorption detection system for capillary liquid chromatography, said system comprising:
    an LED for generating a UV light;
    a first lens for receiving and focusing the UV light from the LED;
    a band-pass filter for filtering the UV light from the first lens;
    a second lens for receiving and focusing the UV light from the band-pass filter;
    at least one slit for passing the UV light received from the second lens and disposed for reducing stray light from entering a capillary column, wherein the slit is less than the width of the internal diameter of the capillary column;
    the capillary column for receiving the UV light passed through the at least one slit, the capillary column positioned so that the UV light passes through a cross section thereof to perform on-column detection; and
    a detector for receiving the UV light that has passed through the capillary column and performing capillary liquid chromatography without knowing path length of the UV light.

2. The system as defined in claim 1 wherein the detection system is further comprised of a system for analyzing absorption of the UV light by at least one compound disposed in a liquid within the capillary column by analyzing the UV light that is received by the detector.

3. The system as defined in claim 1 wherein the detector is further comprised of a smoothing system for processing data received by the detector in order to reduce noise from the detection system.

4. The system as defined in claim 3 wherein the smoothing system is selected from the group of smoothing systems comprised of: smoothing by averaging over a fixed window, smoothing by averaging over a sliding window of fixed width, smoothing using an exponentially weighted moving average, and smoothing using a causal or non-causal filter constructed to whiten the baseline noise process.

5. The system as defined in claim 3 wherein the detector is further comprised of:
    a photodiode for receiving the UV light from the capillary column;
    an operational amplifier for receiving current from the photodiode and converting it into voltage values; and
    an analog-to-digital converter for receiving the voltage values from the operational amplifier and converting it into digital values.

6. The system as defined in claim 5 wherein the detector is further comprised of an RC filter disposed between the operational amplifier and the analog-to-digital converter for reducing noise in the detection system.

7. The system as defined in claim 3 wherein the smoothing system is further comprised of a smoothing system implemented in hardware.

8. The system as defined in claim 3 wherein the smoothing system is further comprised of a smoothing system implemented in software.

9. The system as defined in claim 1 wherein the detection system is further comprised of a DC power source for providing power to the LED and the detector.

10. A method for performing capillary liquid chromatography using an ultra-violet light emitting diode based UV absorption detection system, said method comprising the steps of:
    providing a light emitting diode (LED) as a source of UV light, a first lens for receiving and focusing the UV light from the LED, a band-pass filter for filtering the UV light from the first lens, a second lens for receiving and focusing the UV light from the band-pass filter, at least one slit for passing the UV light received from the second lens and disposed for reducing stray light from entering a capillary column, the capillary column for receiving the UV light passed through the at least one slit, the capillary column positioned so that the UV light passes through a cross section thereof to perform on-column detection, wherein the slit is less than the width of the internal diameter of the capillary column, and a detector for receiving the UV light that has passed through the capillary column;
    generating the UV light from the LED;
    measuring the UV light that passes through the capillary column by using the detector; and analyzing absorption of the UV light by at least one compound disposed in a liquid within the capillary column by analyzing the UV light that is received by the detector and performing capillary liquid chromatography without knowing path length of the UV light.

11. The method as defined in claim 10 wherein the method further comprises the step of maximizing an amount of the UV light that passes through the capillary column by using a stable UV light source and eliminating the need for a reference signal that may be created by a beam splitter that splits the UV light from the LED.

12. The method as defined in claim 11 wherein the method further comprises the step of increasing the amount of the UV light received by the detector by at least two orders of magnitude.

13. The method as defined in claim 10 wherein the method further comprises the steps of:
selecting a wavelength of the UV light generated by the LED; and
selecting the band-pass filter to match the wavelength of the UV light generated by the LED to thereby reduce stray light from reaching the capillary column.

14. The method as defined in claim 10 wherein the method further comprises the step of positioning the second lens relative to the first lens such that a focal point of the UV light from the second lens is equal to or less than an inside diameter (ID) of the capillary column.

15. The method as defined in claim 10 wherein the method further comprises the step of reducing stray light that passes into the capillary column by:
providing the band-pass filter between the first lens and the second lens; and
providing at least one slit between the second ball lens and the capillary column.

16. The method as defined in claim 10 wherein the method further comprises the step of improving peak shapes and increasing detection sensitivity.

17. The method as defined in claim 10 wherein the method further comprises the step of reducing noise in the detection system by performing smoothing of data received by the detector.

18. The method as defined in claim 10 wherein the method further comprises the step of providing a photodiode for receiving the UV light from the capillary column, providing an operational amplifier for receiving current from the photodiode and converting it into voltage values, and providing an analog-to-digital converter for receiving the voltage values from the operational amplifier and converting it into digital values that are recordable.

19. The method as defined in claim 18 wherein the method further comprises the step of disposing an RC filter between the operational amplifier and the analog-to-digital converter to thereby reduce noise in the detection system.

20. The method as defined in claim 19 wherein the method further comprises the step of reducing noise in the detection system by performing software smoothing of data received by the detector.

21. The method as defined in claim 19 wherein the method further comprises the step of reducing noise in the detection system by performing smoothing of data received by the detector using a hardware system.

22. The method as defined in claim 10 b wherein the method further comprises the step of providing power to the LED and the detector of the detection system using a DC power source to thereby enable the detection system to be portable.

23. A method for performing capillary liquid chromatography using an ultra-violet light emitting diode based UV absorption detection system, said method comprising the steps of:
providing a light emitting diode (LED) as a source of UV light, a double lens system for receiving and focusing the UV light from the LED, a band-pass filter for filtering the UV light from the LED, at least one slit for passing the UV light received from the second lens and reducing the passage of stray light, a capillary column for receiving the UV light passed through the at least one slit, the capillary column positioned so that the UV light passes through a cross section thereof to perform on-column detection, wherein the slit is less than the width of the internal diameter of the capillary column, and a detector for receiving the UV light that has passed through the capillary column;
generating the UV light from the LED and eliminating the need for a reference UV light because the LED is a stable UV light source;
measuring the UV light that passes through the capillary column by using the detector and performing capillary liquid chromatography without knowing path length of the UV light; and
reducing noise from the detector by smoothing data collected from analyzing absorption of the UV light by at least one compound disposed in a liquid within the capillary column by analyzing the UV light that is received by the detector.

24. A method for performing capillary liquid chromatography using a portable ultra-violet light emitting diode based UV absorption detection system, said method comprising the steps of:
providing a light emitting diode (LED) as a source of UV light, a first lens for receiving and focusing the UV light from the LED, a band-pass filter for filtering the UV light from the first lens, a second lens for receiving and focusing the UV light from the band-pass filter, at least one slit for passing the UV light received from the second lens and disposed for reducing stray light from entering a capillary column, the capillary column for receiving the UV light passed through the at least one slit, the capillary column positioned so that the UV light passes through a cross section thereof to perform on-column detection, wherein the slit is less than the width of the internal diameter of the capillary column, a detector for receiving the UV light that has passed through the capillary column and a power source that provides a DC power source;
generating the UV light from the LED using the DC power source;
measuring the UV light that passes through the capillary column by using the detector that operates using the DC power source and performing capillary liquid chromatography without knowing path length of the UV light; and
analyzing absorption of the UV light by at least one compound disposed in a liquid within the capillary column by analyzing the UV light that is received by the detector.

* * * * *